United States Patent [19]
Lee

[11] Patent Number: 6,024,724
[45] Date of Patent: Feb. 15, 2000

[54] LIQUID MEDICINE INJECTION DEVICE

[76] Inventor: Young Gyu Lee, Han-Jin Apt. 204-1807, 616-100 DonAm-Dong, SungBuk-ku, Seoul 136-060, Rep. of Korea

[21] Appl. No.: 09/034,226

[22] Filed: Mar. 4, 1998

[30] Foreign Application Priority Data

Jun. 19, 1997 [KR] Rep. of Korea ...................... 97-25681
Oct. 21, 1997 [KR] Rep. of Korea ...................... 97-53948

[51] Int. Cl.[7] .................................................. A61M 37/00
[52] U.S. Cl. ........................................... 604/132; 604/131
[58] Field of Search ..................................... 604/132, 131

[56] References Cited

U.S. PATENT DOCUMENTS

| | | | |
|---|---|---|---|
| 3,468,308 | 9/1969 | Bierman | 604/132 X |
| 3,993,069 | 11/1976 | Buckles et al. | 604/132 |
| 4,909,790 | 3/1990 | Tsujikawa et al. | 604/132 |
| 5,178,610 | 1/1993 | Tsujikawa et al. | 604/132 |
| 5,211,632 | 5/1993 | Tsukada | 604/132 |

FOREIGN PATENT DOCUMENTS

9012609 11/1990 WIPO ..................................... 604/132

Primary Examiner—Jeffrey A. Smith

[57] ABSTRACT

A liquid medicine injection device have a two-way injection amount controller. A collapsible tube is expanded with liquid medicine and forcibly discharges the medicine without allowing the medicine to remain in the tube due to the pressure of the fully expanded tube, thus preventing waste of the expensive medicine. The device, via the two-way injection amount controller, normally injects a primarily controlled amount of medicine into a patent at a steady rate and selectively and temporarily allows confluent medicine to join the primarily controlled amount of medicine in accordance with a patient's condition without giving additional syringe pain to the patient.

12 Claims, 4 Drawing Sheets

LIQUID MEDICINE INJECTION DEVICE

BACKGROUND OF THE INVENTION

1. Field of the Invention

The present invention relates, in general, to a device for giving an injection of liquid medicine to a patient and, more particularly, to a controllable liquid medicine injection device capable of normally giving an injection of a predetermined amount of liquid medicine, such as a special anodyne or antibiotic, to a patient at a constant rate and selectively and temporarily allowing confluent medicine to join the primarily injected medicine, thus increasing the amount of injected medicine in accordance with a patient's condition, thus improving medicinal effect.

2. Description of the Prior Art

In the medical field, it is necessary to continuously give a special antibiotic to a person having cancer or leukemia and periodically, a special anodyne to a person suffering from post-operative pain.

In the event of special liquid medicines, such as antibiotics for sufferers of cancer or leukemia, medicine has to be normally and steadily given to a sufferer in very small amounts, which is different from general medicine. In addition, it is often required to temporarily increase the amount of injected medicine in accordance with a patient's condition. In an effort to achieve the above object, an injection hose with a manual controller is proposed. In order to control the amount of special liquid medicine passing through such an injection hose, a medical personnel, such as a doctor or a nurse, manually handles the controller while observing a controlled amount of medicine in the transparent hose. However, such a manual controller fails to precisely control the amount of liquid medicine to be given to a patient, thus forcing a medical team to repeatedly adjust the amount of medicine. Therefore, known medicine injection devices with such controllers are inconvenient to both medical teams and patients and reduce medicinal effect.

In particular, when a medical team unconsciously adjusts the manual controller to give an injection of an excessive amount of medicine to a patient, the excessive amount of medicine may cause the patient to fall into a coma or into shock death, On the contrary, when a manually controlled amount of medicine is less than an effective amount, the medicinal effect on the patient is reduced.

Sometimes, it is necessary to give another liquid medicine, such as an anodyne, to a patient when a special medicine, such as an antibiotic, is already being given to the patient using an injection hose. In this case, the other medicine or the anodyne may be directly injected into a vein using a syringe being pricked into the vein or indirectly injected into the vein with a syringe being pricked into the existing injection hose. However, the direct injection of an anodyne into a vein wastes labor of a medical team and gives additional pain to the patient, making the patient unstable. On the other hand, when the anodyne is indirectly injected into a vein with a syringe being injected into the existing injection hose, the syringe forms a syringe hole on the hose, thus causing leakage of liquid medicine from the hose through the syringe hole. Such a syringe hole may also cause infiltration of infectious bacteria into the hose. Therefore, both the injection hose and the liquid medicine have to be frequently changed with new hoses and medicine, thus being inconvenient to both a patient and a medical team.

When a liquid medicine is injected into a vein of a patient with a syringe, the amount of medicine to be injected is influenced by a pressing force applied onto the piston of the syringe so that an excessive amount of medicine may be unconsciously injected into the vein and may cause the patient to fall into a coma or into shock death.

Meanwhile, an injection pump may be used for injecting a liquid medicine into a vein of a patient. However, such an injection pump prevents the patient from moving and causes a safety alarm device of medical equipment to frequently generate a voice alarm signal, irritating to the patient and those around the patient.

SUMMARY OF THE INVENTION

Accordingly, the present invention has been made keeping in mind the above problems occurring in the prior art. An object of the present invention is to provide a controllable liquid medicine injection device which allows a predetermined amount of liquid medicine, such as a special antibiotic, to be steadily injected into a vein of a patient suffering from, for example, cancer or leukemia, at a steady rate, thus improving medicinal effect, and selectively and temporarily allows confluent medicines to join the primarily injected medicine without using any additional syringe, thus increasing the amount of injected medicine in accordance with a patient's condition.

In order to accomplish the above object, the present invention provides a liquid medicine injection device, comprising: a medicine container encased by a casing and adapted for temporarily containing liquid medicine and selectively and completely discharging the medicine under pressure without allowing the medicine to remain in the container, thus injecting the medicine into a patient; a first three way check valve connected to the outlet of the container with a discharging hose being connected to the outlet of the three way check valve, the first three way check valve being adapted for selectively introducing liquid medicine into the container from the outside or dispensing the medicine from the container through the discharging hose; and an injection amount controller connected to the discharging hose, the controller being adapted for controlling the medicine, thus normally injecting a precisely controlled amount of medicine into the vein at a steady rate and selectively and temporarily injecting confluent medicine together with the primary precisely controlled amount of medicine into the vein.

BRIEF DESCRIPTION OF THE ACCOMPANYING DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
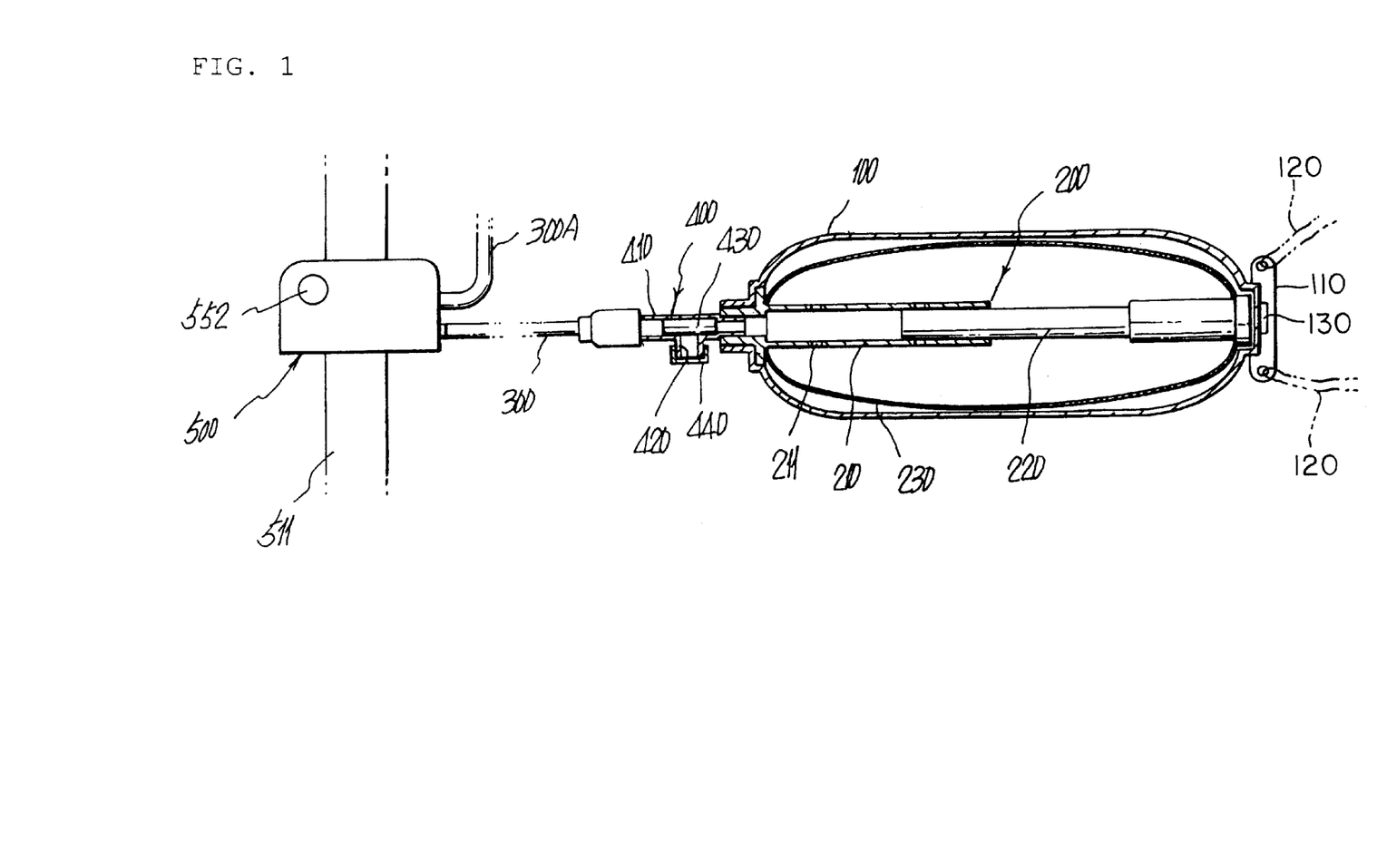
FIG. 1 is a sectional view of a liquid medicine injection device in accordance with the primary embodiment of the present invention.

FIG. 1 is a sectional view of a liquid medicine injection device in accordance with the primary embodiment of the present invention. As shown in the drawing, the liquid medicine injection device of this invention is comprised of a medicine container 200. The container 200 is encased by a hard casing 100. The above casing 100 is provided with a connection member 110 at one end thereof for connecting a hanging loop 120 to the casing 100. The connection member 110 is holed at its center, thus forming a holder 130 for holding a clip (not shown). The container 200 temporarily contains a liquid medicine and selectively and completely discharges the medicine under pressure without allowing the medicine to remain in the container 200. A liquid medicine discharging hose 300 is connected to the outlet of the container 200 with a first three way check valve 400 being interposed between the container 200 and the hose 300. The first three way check valve 400 allows a liquid medicine to be introduced into the container 200 from the outside or dispensed from the container 200 through the hose 300. The hose 300 extends from the three way check valve 400 to a length, thus being connected to an injection amount controller 500. The controller 500 also has a flexible hose 300A and allows a precisely controlled amount of medicine to be injected into a vein of a patient at a constant rate, with both the hose 300A being attached to an arm of the patient and a syringe (not shown) being pricked into the vein. The controller 500 also temporarily contains confluent medicine prior to selectively and forcibly injecting the confluent medicine together with the primarily injected medicine into the vein as desired.

Figure 2A:
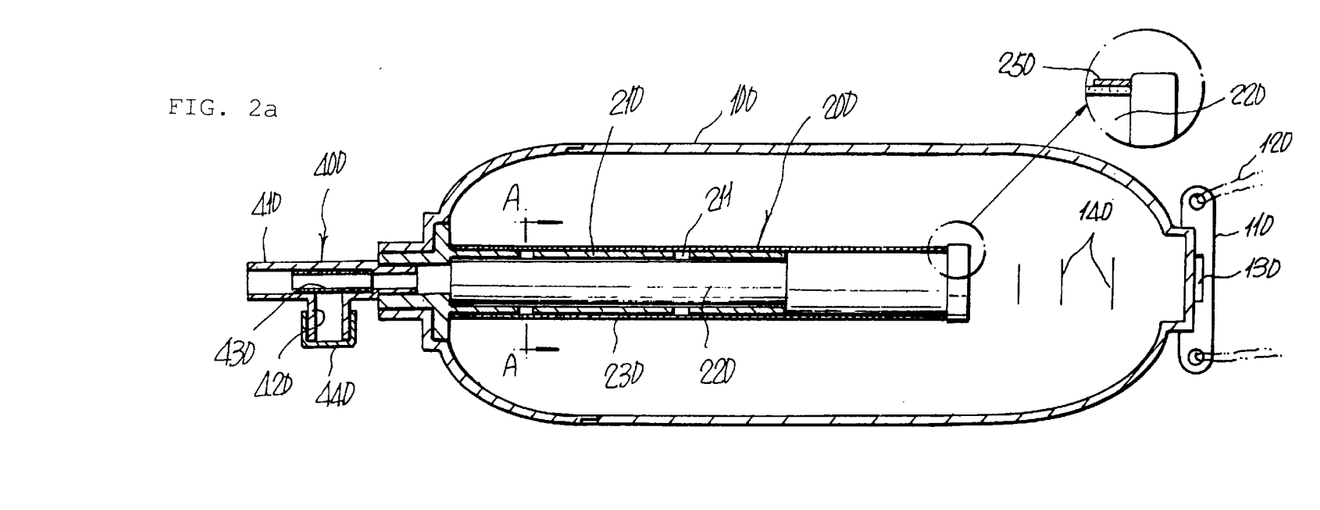
FIG. 2a is an enlarged sectional view of a liquid medicine container of the injection device according to this invention, showing the container in an empty state.
Figure 2B:
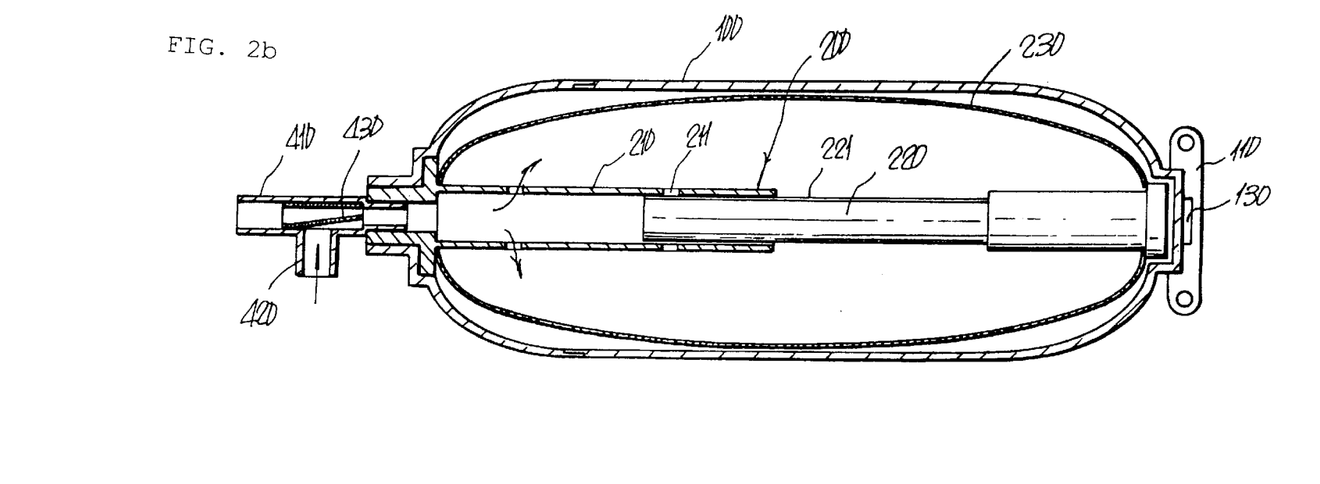
FIG. 2b is a view corresponding to FIG. 2a, but showing the container filled with a liquid medicine.

FIGS. 2a and 2b show the construction of the container 200 in detail. The container 200 has a telescopic pipe structure comprised of a fixed hollow pipe 210 and a movable solid pipe 220. The fixed hollow pipe 210 is fixedly and axially installed in the case 100 with the outside end of the pipe 210 being tightly set in the projecting mouth of the case 100. The fixed pipe 210 has a plurality of radial holes 211, through which the interior of the pipe 210 communicates with the interior of a collapsable tube 230 as will be described later herein. The solid pipe 220 is movably inserted into the inside end of the fixed hollow pipe 210 so that the solid pipe 220 is axially movable in relation to the hollow pipe 210. The collapsable tube 230 is received in the casing 100 and is integrated with the remote ends of the two pipes 210 and 990 at both ends. The collapsable tube 230 is selectively expanded with liquid medicine or discharges the medicine under pressure to the outside.

In the casing 100 a rubber ring 250, having a predetermined elasticity, is tightly fitted over the collapsable tube 230 at the end where the collapsable tube 230 is fitted over the movable pipe 220. The rubber ring 250 tightens the end of the collapsable tube 230 on the movable pipe 220, thus preventing the collapsable tube 230 from being unexpectedly removed from the movable pipe 220 during a movement of the pipe 220.

Figure 3:
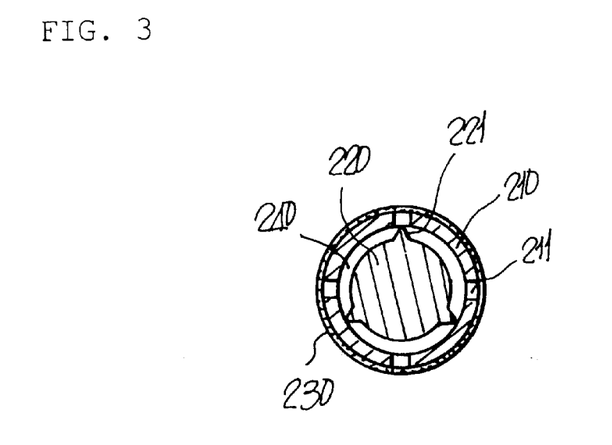
FIG. 3 is a cross-sectional view taken along the line A—A of FIG. 2a, showing a telescopic pipe structure installed in the medicine container of this invention.

In order to allow the liquid medicine to be smoothly introduced into or discharged from the container 200 through the fixed pipe 210, a plurality of regularly spaced axial rails 221 are formed on the solid pipe 220, thus forming a plurality of axial channels 240 at the junction between the two pipes 210 and 220 as shown in FIG. 3. In order to allow a user to check the amount of medicine in the container 200, the casing 100 is made of a transparent material and has a graduated scale 140 on the outside surface.

Each of the axial rails 221 of the solid pipe 220 preferably has a wedge cross-section as shown in FIG. 3 so that the frictional contact area between each rail 221 and the interior wall of the hollow pipe 210 is effectively reduced, thus allowing the movable pipe 220 to be smoothly movable relative to the fixed pipe 210. Of course, it should be understood that each rail 221 may have a semicircular cross-section in place of the wedge cross-section.

In the first three way check valve 400, a horizontal pipe part 410 and a vertical pipe part 420 are integrated together into a T-shaped single pipe structure. One end of the horizontal part 410 is tightly fitted into the outside end of the fixed hollow pipe 210, while the other end is connected to the hose 300. The vertical pipe part 420 allows the medicine to pass through it prior to filling the container 200. The three way check valve 400 also has an elastic hollow pipe 430, which is made of silicon or rubber and is received in the horizontal pipe part 410 at a position around the cross of the valve 400. When liquid medicine under pressure is discharged from the container 200 into the hose 300, the elastic pipe 430 comes into close contact with the interior wall of the horizontal pipe part 410 while blocking the vertical pipe part 420, thus allowing the medicine to effectively flow from the container 200 into the hose 300. Meanwhile, when liquid medicine under pressure is introduced into the container 200 from the outside, the pressure of the inlet medicine pushes the elastic pipe 430 as shown in FIG. 2b, thus allowing the vertical pipe part 420 to communicate with the fixed pipe 210 of the container 200 and leading the medicine into the collapsable tube 230 through both the vertical pipe part 430 and the fixed pipe 210.

A screw cap 440 removably engages with the lower end of the vertical pipe part 420 of the three way check valve 400 so that the cap 440 normally closes the vertical pipe part 420 in order to completely prevent unexpected infiltration of infectious bacteria into the valve 400 and selectively opens the part 420, when it is necessary to fill the container 200 with liquid medicine.

Figure 4:
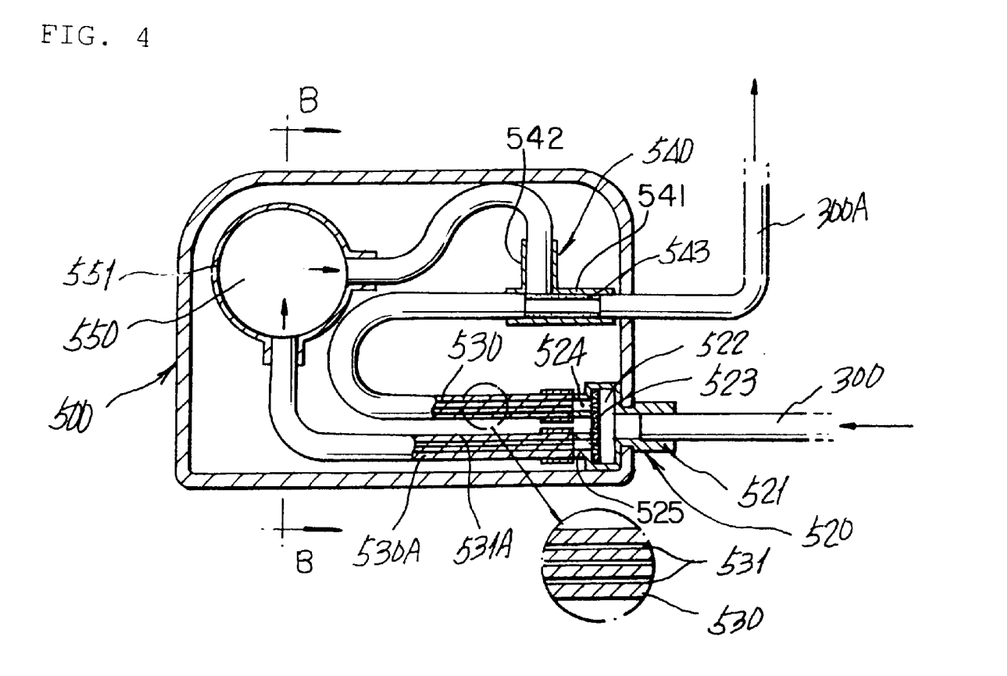
FIG. 4 is a sectional view showing the construction of an injection amount controller of the device of this invention.
Figure 5:
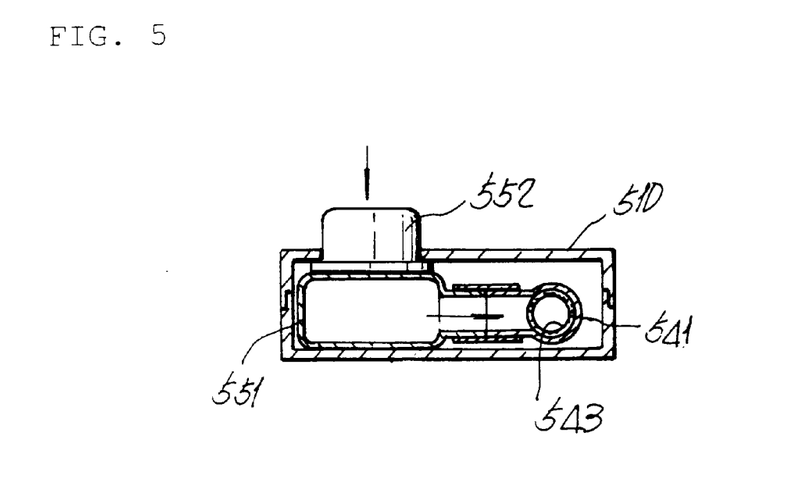
FIG. 5 is a sectional view of the injection amount controller taken along the line B—B of FIG. 4.

FIG. 4 is a sectional view showing the construction of the injection amount controller 500 and FIG. 5 is a sectional view of the controller 500 taken along the line B—B of FIG. 4. As shown in the drawings, the injection amount controller 300 is comprised of a housing 510 with a band 511 (FIG. 1). The housing 510 has upper and lower parts. A three way filter member 520 is set in the housing 510 at a position where the hose 300 is connected to the housing 510. The member 520 filters impurities from the liquid medicine which is introduced into the member 520 from the hose 300 and dispenses the medicine into two control pipes 530 and 530A. The two control pipes 530 and 530A are connected to branched outlets of the member 520 and controllably feed the liquid medicine free from impurities. Connected to the first control pipe 530 is a second three way check valve 540. The controller 500 also has a confluence means 550, which is connected to both the second pipe 530A and the vertical pipe part 542 of the three way check valve 540, thus temporarily containing confluent medicine and selectively allowing the confluent medicine to join the primarily injected medicine at the second three way check valve 540 in accordance with conditions of the patient.

The three way filter 520 is connected to the hose 300 through a connection pipe part 521 and has a medicine containing cavity 522 with a filter 523 being set at the junction between the cavity 522 and the two branched outlets 524 and 525. The filter 523 filters impurities from the liquid medicine when the medicine passes from the cavity 522 into the two branched outlets 524 and 525.

Each of the two control pipes 530 and 530A, connected to the outlets 524 and 525, has a plurality of capillary tubes 531, 531A. Each of the capillary tubes 531 and 531A has a fine size suitable for feeding the liquid medicine while controlling the amount of medicine. The size of each capillary tube 531A of the second pipe 530A is relatively larger than that of each capillary tube 531 of the first pipe 530 so that the liquid medicine is filled in the confluence means 550 over a predetermined time.

In the second three way check valve 540, a horizontal pipe part 541 and a vertical pipe part 542 are integrated together into a T-shaped single pipe structure. One end of the horizontal part 541 of the valve 540 is tightly connected to the first control pipe 530, while the other end is connected to the hose 300A. The vertical pipe part 542 is connected to the confluence means 550, thus allowing the confluent medicine of the means 550 to selectively join the primarily injected medicine of the horizontal pipe part 541. The second three way check valve 540 also has an elastic hollow pipe 543, which is received in the horizontal pipe part 541 at a position around the juncture of the valve 540. When the liquid medicine passes from the first control pipe 530 into the hose 300A through the horizontal pipe part 541, the elastic pipe 543 comes into close contact with the interior wall of the horizontal pipe part 541 while blocking the vertical pipe part 542, thus allowing the primarily injected medicine to effectively flow in the horizontal pipe part 541.

The confluence means 550 has an expandable tank 551, which is connected to both the second control pipe 530A and the second three way check valve 540, thus temporarily containing the confluent liquid medicine. The confluence means 550 also has a push button 552, which is positioned on the top of the tank 551 with the top end of the button 552 projecting from the top wall of the housing 510. The button 552 is used for selectively compressing the internal pressure of the tank 551 when it is necessary to discharge the confluent medicine from the tank 551 into the horizontal pipe part 541.

In the injection device of this invention, it is preferable to connect both the discharging hose 300 and the flexible hose 300A to the housing 510 of the controller 500 at the same side wall of the housing 500, thus preventing the flexible hose 300A from disturbing a patient with the housing 500 being worn on a wrist with the band 511.

The operational effect of the above liquid medicine injection device will be described hereinbelow.

When the container 200 is in an empty state, the collapsable tube 230 is fully collapsed so that the movable solid pipe 220 is fully retracted into the fixed hollow pipe 210 as shown in FIG. 2a.

In order to fill the above empty container 200 with a liquid medicine, the screw cap 440 is loosened and separated from the vertical pipe part 420 of the first three way check valve 400 prior to connecting a hose of an outside medicine source (not shown) to the vertical pipe part 420. The medicine source is, thereafter, compressed so as to forcibly introduce the medicine under pressure into the vertical pipe part 420. When the medicine under pressure is introduced into the vertical pipe part 420, the pressure of the medicine pushes the silicon elastic pipe 430 as shown by the dotted line of FIG. 2b, thus allowing the vertical pipe part 420 to communicate with the fixed pipe 210. The liquid medicine under pressure is, thus, introduced into the fixed pipe 210 while pushing the movable pipe 220 so that the movable pipe 220 extends from the fixed pipe 210. Therefore, the collapsable tube 230 with both ends being integrated with the remote ends of the two pipes 210 and 220 expands, while the interior of the fixed pipe 210 communicates with the interior of the collapsable tube 230 through the radial holes 211 of the fixed pipe 210. The collapsable tube 230 is thus expanded with the liquid medicine.

When the liquid medicine is introduced into the collapsable tube 230 as described above, the tube 230 is stably expanded without being unexpectedly removed from the movable pipe 220 due to the rubber ring 250 which tightly fixes the end of the tube 230 on the movable pipe 220.

The expanded tube 230, filled with the liquid medicine, is shown in FIG. 2b. In such an expanded tube 230, the amount of liquid medicine is easily measured by the graduated scale 140 of the transparent casing 100.

When a predetermined amount of liquid medicine is completely filled in the tube 230, the hose of the medicine source is removed from the vertical pipe part 420 of the first valve 400 before the lower end of the vertical pipe part 420 is tightly closed by the screw cap 440. When the vertical pipe part 420 is closed by the cap 440, the elastic pipe 430 is returned to its original state so that the pipe 430 comes into close contact with the interior wall of the horizontal pipe part 410 while blocking the vertical pipe part 420. Therefore, the medicine of the horizontal pipe part 410 is prevented from leaking from the valve 400 through the vertical pipe part 420.

When it is necessary to controllably inject the liquid medicine of the tube 230 into a vein of a patient, a medical personnel pricks the vein with a syringe (not shown) of the hose 300A prior to fixing the position of the syringe on an arm of the patient using a band. Thereafter, the band 511 of the injection amount controller 500 is tightened around the wrist of the patient so that the controller 500 is stably positioned on the wrist.

When the patient lies in bed, the casing 100 of the device is preferably hung on a movable or fixed hanger (not shown), which is positioned around the bed, with a hanging loop 120 being connected to the connection member 110 of the casing 100. The casing 100 may be also hung around the neck of a patient with the loop 120 when the patient moves. In such a case, the casing 100 is preferably clipped on the clothes of the patient using the clip of the holder 130, thus allowing the patient or a person around the patient to be free from taking the casing 100 with one's hand and being convenient to users.

When the injection device is attached to a patient as described above, a pressure is generated in the fully expanded tube 230, thus causing the liquid medicine to be automatically discharged from the tube 230 into the horizontal pipe part 410 of the first three way check valve 400 through the fixed pipe 210 with the radial holes 211. The elastic pipe 430 in the above case comes into close contact with the interior wall of the horizontal pipe part 410 while blocking the vertical pipe part 420 so that the medicine is prevented from flowing in the vertical pipe part 420 but flows into the hose 300 through the elastic pipe 430.

The liquid medicine of the hose 300 is, thereafter, introduced into the cavity 522 of the three way filter 520 through the connection pipe part 521 and passes through the filter 523 so that impurities are removed from the medicine. The medicine free from impurities is discharged from the member 520 through the two branched outlets 524 and 525.

Thereafter, the medicine passes through the fine capillary tubes 531 and 531A of the two control pipes 530 and 530A so that the amount of medicine passing through the control pipes 530 and 530A is controlled by the capillary tubes 531 and 531A.

More particularly the liquid medicine, passing through the fine capillary tubes 531 of the first control pipe 530, is to be directly injected into the vein requiring that the capillary tubes 531 be finely sized so as to allow a precisely controlled amount of medicine to be injected into the vein. Meanwhile, the second control pipe 530A is for leading the confluent medicine into the tank 551 of the confluence means 550 so that the size of each capillary tube 531A of the second control pipe 530A is relatively larger than that of each capillary tube 531 of the first control pipe 530. Therefore, the confluent medicine is completely filled in the tank 551 over time.

The precisely controlled amount of liquid medicine of the first control pipe 530 passes through the horizontal pipe part 541 of the second three way check valve 540 and the hose 300A in order prior to being injected into the vein with the syringe. The elastic pipe 543 in the above case comes into close contact with the interior wall of the horizontal pipe part 541 while blocking the vertical pipe part 542 due to its elasticity so that the precisely controlled amount of liquid medicine is prevented from leaking into the vertical pipe part 542 but is allowed to be injected into the vein at a steady rate.

The liquid medicine of the cavity 522 of the three way filter 520 is also discharged from the cavity 522 through the second outlet 525 and passes through the capillary tubes 531A of the second control pipe 530A. In this case, the amount of medicine is controlled by the capillary tubes 531A. The medicine of the second control pipe 530A or the confluent medicine is contained in the tank 551 of the confluence means 550.

When the precisely controlled amount of liquid medicine of the first control pipe 530 is injected into the vein at a constant rate, it may be necessary to temporarily increase the amount of medicine in accordance with conditions of the patient. In this case, the button 552 of the confluence means 550 is pressed by a medical personnel, thus compressing the internal pressure of the tank 551 expanded with the confluent liquid medicine and allowing the confluent medicine under pressure to be forcibly introduced into the horizontal pipe part 541 through the vertical pipe part 542. The elastic pipe 543 in the above state is biased by the pressure of the confluent medicine so that the two pipe parts 541 and 542 communicate together. The confluent medicine of the tank 551 thus joins the precisely controlled amount of medicine of the first control pipe 530 together in the horizontal pipe part 541 prior to being injected into the vein of the patient.

When the confluent medicine of the confluence means 550 is completely injected into the vein while joining the medicine of the first control pipe 530, the external pressure is removed from the button 552 so that the vertical pipe part 542 is free from the pressure of the confluent medicine and causes the elastic pipe 543 to be elastically returned to its original state, where the pipe 543 is brought into close contact with the interior wall of the horizontal pipe part 541 and blocks the vertical pipe part 542. Thus, the injection device is returned from the confluence mode to a normal mode, where only the precisely controlled amount of medicine, passing through the capillary tubes 531 of the first control pipe 530, is injected into the vein. Meanwhile, the empty tank 551 of the confluence means 550 is filled with new confluent medicine through the second control pipe 530A at a slow rate. In this case, the capillary tubes 531A of the second control pipe 530A only allow a very small amount of medicine to pass through, thus requiring considerable time for filling the empty tank 551 with new confluent medicine. The capillary tubes 531A thus prevent an excessive amount of liquid medicine from being unconsciously injected into the vein just after a primary confluence of the liquid medicine. Therefore, the injection device of this invention almost completely prevents the patient from falling into a coma or shock death caused by an excessive amount of medicine.

When the liquid medicine is continuously injected into the vein using the device of this invention as described above, the amount of medicine in the collapsable tube 230 is gradually reduced, causing a shrinkage of the tube 230. The movable solid pipe 220 is thus retracted into the fixed hollow pipe 210 so that the pipe 220 is positioned around the radial holes 211 of the fixed pipe 210. However, the interior of the fixed hollow pipe 210 in the above state effectively communicates with the interior of the tube 230 through the holes 211 because the axial channels 240 are formed at the junction between the internal wall of the fixed wall 210 and the external wall of the movable pipe 220 due to the axial rails 221 of the movable pipe 220. Therefore, the liquid medicine remaining in the tube 230 is completely discharged into the fixed pipe 210. When the tube 230 is completely emptied, the movable pipe 220 is fully retracted into the fixed pipe 210 with the tube 230 being brought into close contact with the external wall of the fixed pipe 210 as shown in FIG. 2a so that the medicine does not remain in the tube 230, thus preventing waste of the expensive medicine.

Figure 6:
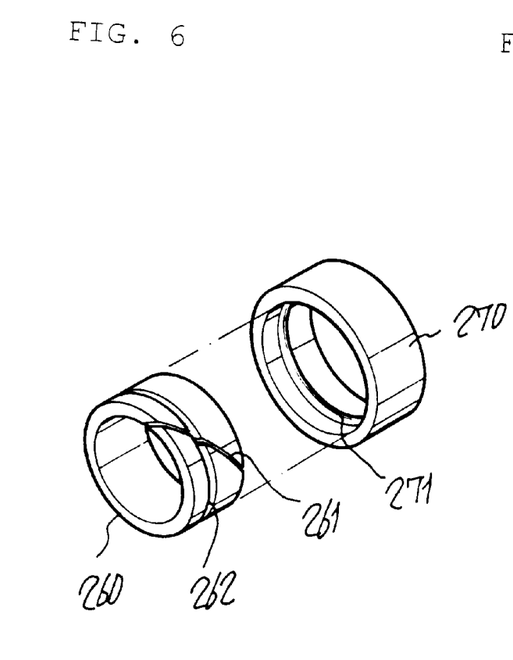
FIG. 6 is an exploded perspective view showing a coupling structure used for fixing the edge of a collapsable tube to one end of a movable pipe in accordance with another embodiment of the present invention.
Figure 7:
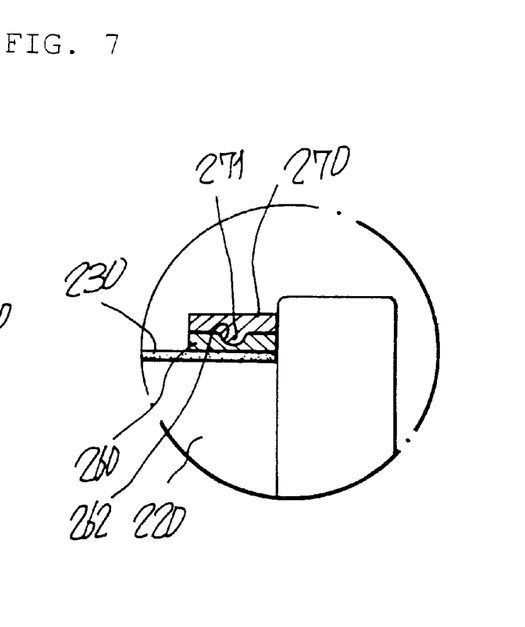
FIG. 7 is a sectional view of the coupling structure of FIG. 6.

FIGS. 6 and 7 show the construction of a coupling structure for fixing the edge of the collapsable tube 230 to the end of the movable pipe 220 in accordance with another embodiment of the present invention. As shown in the drawings, the coupling structure is comprised of two rings, that is, inner and outer rings 260 and 270. The inner ring 260 is tightly fitted over the end of the movable pipe 220, with the edge of the collapsable tube 230 being interposed between the movable pipe 220 and the ring 260. The side wall of the inner ring 260 is cut at an angle of inclination, thus forming an inclined slit 261 allowing the diameter of the ring 260 to be elastically enlarged prior to being fitted over the end of the movable pipe 220. The inner ring 260 also has an annular fitting groove 262 at the center of its outside wall. Meanwhile, the outer ring 270 has an annular fitting rail 271 at the center of its inside wall. The outer ring 270 is fitted over the inner ring 260, with the fitting rail 271 engaging with the fitting groove 262.

In order to fix the edge of the collapsable tube 230 to the end of the movable pipe 220, the edge of the tube 230 covers the end of the pipe 220 prior to fitting the inner ring 260 over the tube 230 at the end of the pipe 220. The inner ring 260, with the slit 261, is primarily expanded so as to enlarge the diameter prior to being fitted over the tube 230 at the end of the pipe 220. When the ring 260 is completely positioned on the tube 230, the expanded ring 260 is elastically constricted due to its elasticity, thus being stably positioned on the tube 230 at the end of the pipe 220 and primarily fixing the edge of the tube 230 to the end of the pipe 220.

Thereafter, the outer ring 270 is fitted over the inner ring 260 with the fitting rail 271 of the outer ring 270 being brought into engagement with the fitting groove 262 of the inner ring 260. The outer ring 270 in the above state compresses the inner ring 260, thus allowing the inner ring 260 to finally fix the edge of the tube 230 to the end of the movable pipe 220. The above coupling structure effectively prevents the edge of the tube 230 from being unexpectedly removed from the end of the movable pipe 220 even when the tube 230 is excessively expanded with liquid medicine.

As described above, the present invention provides a controllable liquid medicine injection device. In the device, a collapsable tube is expanded with liquid medicine, such as an antibiotic or anodyne, and forcibly discharges the medicine without allowing the medicine to remain in the tube due to the pressure of the fully expanded tube, thus preventing waste of the expensive medicine. The device also allows a precisely controlled amount of liquid medicine to be injected into a vein at a steady rate so that the device improves medicinal effect while being free from safety hazards due to an unexpected injection of an excessive amount of medicine. Another advantage of the device resides in that it selectively and temporarily allows confluent medicine to join the primarily injected medicine without using any additional syringe, thus effectively increasing the amount of injected medicine in accordance with a patient's condition without giving additional syringe pain to the patient.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A liquid medicine injection device, comprising:

a casing provided at one end thereof with a connection member for allowing a hanging loop to be connected to said casing, said connection member being holed at its center portion and forming a holder for holding a clip;

a medicine container encased by said casing and adapted for temporarily containing liquid medicine and selectively and completely discharging the liquid medicine such that the liquid medicine does not remain in said medicine container, thereby injecting the liquid medicine toward a part of the human body;

a first three way check valve connected to an outlet of said medicine container with a discharging hose connected to an outlet of said first three way check valve and adapted for selectively introducing the liquid medicine into said medicine container from outside or dispensing the liquid medicine from said medicine container through said discharging hose; and an injection amount controller connected to said discharging hose and adapted for controlling an amount of the liquid medicine injected into the part of the human body, said injection amount controller normally injecting a precisely primary controlled amount of the liquid medicine into the part of the human body at a steady rate and selectively and temporarily injecting confluent liquid medicine together with the precisely primary controlled amount of the liquid medicine into the part of the human body;

said injection amount controller including
a housing,
a three way filter member positioned in said housing and adapted for filtering impurities from the liquid medicine prior to dispensing the liquid medicine into two branched passages,
first and second control pipes connected to said two branched passages, respectively, and feeding the liquid medicine while controlling the amount of the liquid medicine,
a second three way check valve connected to said first control pipe, and
confluence means, connected to both said second control pipe and said second three way check valve, for temporarily receiving confluent liquid medicine through said second control pipe and selectively allowing the confluent liquid medicine to join the primary control led amount of the liquid medicine flowing through said first control pipe, thus increasing the amount of liquid medicine injected into the part of the human body.

2. The liquid medicine injection device according to claim 1, wherein said container comprises:

a hollow pipe fixedly and axially installed in said case with an outside end of said hollow pipe being tightly set in a mouth of the case, said hollow pipe having a plurality of radial holes;

a solid pipe movably inserted into an inside end of said hollow pipe, thus being axially movable in relation to the hollow pipe; and a collapsible tube received in said casing and integrated with remote ends of said hollow and solid pipes, said collapsible tube being selectively expanded with liquid medicine or discharging the medicine under pressure into the first three way check valve.

3. The liquid medicine injection device according to claim 2, wherein a plurality of regularly spaced axial rails are positioned on the solid pipe, for forming a plurality of axial channels at the junction between the hollow and solid pipes and allowing the liquid medicine to be smoothly introduced into or discharged from the container through the hollow pipe, and allowing the solid pipe to smoothly move relative to the hollow pipe.

4. The liquid medicine injection device according to claim 2, further comprising a coupling structure to integrate said collapsible tube with said solid pipe, said coupling structure including an inner ring fitted over one end of the solid pipe with an edge of the collapsible tube being interposed between the inner ring and the solid pipe, said inner ring having an annular fitting groove at a center of an outer surface and being cut at a side wall, thus forming a slit allowing the diameter of the inner ring to be enlarged prior to being fitted over the one end of the solid pipe; and an outer ring having an annular fitting rail at a center of an inside wall, said outer ring being fitted over said inner ring with said annular fitting rail engaging with said fitting groove of the inner ring.

5. The liquid medicine injection device according to claim 1, wherein said first three way check valve comprises:

a horizontal hollow pipe part allowing the medicine to pass through;

a vertical pipe part integrated with said horizontal pipe part into a single pipe structure and adapted for introducing the medicine into the container; and an elastic hollow pipe received in said horizontal pipe part at a position around a cross position of the valve, said elastic hollow pipe normally coming into close contact with an interior wall of horizontal pipe part while blocking the vertical pipe part, thus allowing the medicine to be discharged from the container into the discharging hose through the horizontal pipe part and being selectively pushed by pressure of inlet medicine, thus allowing the medicine to be introduced into the container from the outside.

6. The liquid medicine injection device according to claim 1, wherein said three way filter member comprises:
   a connection pipe part connecting said filter member to said discharging hose;
   a medicine containing cavity communicating with the connection pipe part and adapted for containing the medicine;
   a medicine filter provided at a junction between said cavity and said two branched passages and adapted for filtering impurities from the medicine; and
   two branched outlets formed at an outlet side of said cavity, thus forming said branched passages.

7. The liquid medicine injection device according to claim 1, wherein said second three way check valve comprises:
   a horizontal pipe part, connected to both the first control pipe and a second hose, to lead the medicine to a syringe through the second hose;
   a vertical pipe part, integrated with the horizontal pipe part into a single pipe structure and connected to said confluence means, for allowing the confluent medicine of said confluence means to selectively join the primary controlled amount of medicine; and
   an elastic hollow pipe received in said horizontal pipe part at a position around a cross portion of the second three way check valve, said elastic hollow pipe normally coming into close contact with an interior wall of the horizontal pipe part while blocking the vertical pipe part, thus allowing the primary controlled amount of medicine to flow in the horizontal pipe part and being selectively pushed by pressure of the confluent medicine, thus allowing the confluent medicine to join the primary controlled amount of medicine.

8. The liquid medicine injection device according to claim 1, wherein said confluence means comprises:
   an expandable tank, connected to both the second control pipe and the second three way check valve, to temporarily contain the confluent medicine; and
   a push button positioned on the top of said tank with a top end of said button projecting from a top wall of said housing, said button being adapted for selectively compressing an internal pressure of said tank.

9. A liquid medicine injection device, comprising:
   (a) a liquid medicine container to temporarily contain and selectively discharge liquid medicine;
   (b) a three-way valve, connected to the liquid medicine container, to selectively introduce the liquid medicine into the container or discharge the liquid medicine from the container; and
   (c) a liquid medicine injection amount controller having an inlet connected to the three-way valve to receive liquid medicine from the container and an outlet to dispense liquid medicine from the controller into the patient, the controller including
      (i) a housing;
      (ii) first and second liquid medicine control conduits connected together at the controller inlet to receive liquid medicine and together at the outlet to dispense liquid medicine, the first conduit providing a primary controlled amount of medicine and the second conduit providing a secondary confluent controlled amount of medicine; and
      (iii) a confluent liquid medicine control device, connected to the second conduit, to selectively and temporarily adjust the amount of confluent liquid medicine flowing through the second conduit to the controller outlet for dispensing both the primary and secondary controlled amount of medicine into the patient.

10. A liquid medicine injection device of claim 9, wherein the liquid medicine injection amount controller further comprises a three-way check valve connected to the first conduit.

11. A liquid medicine injection device of claim 10, wherein the liquid medicine injection amount controller further comprises a three-way filter member positioned in the controller to receive and filter liquid medicine from the inlet of the controller prior to dispensing of the liquid medicine into the first and second conduits.

12. A liquid medicine injection device of claim 9, wherein the confluent liquid medicine controller further comprises a three-way filter member positioned in the controller to receive and filter liquid medicine from the inlet of the controller prior to dispensing of the liquid medicine into the first and second conduits.

* * * * *